United States Patent
Nasif

(10) Patent No.: US 12,402,866 B2
(45) Date of Patent: Sep. 2, 2025

(54) PUNCH BIOPSY APPARATUS AND ASSOCIATED METHOD(S)

(71) Applicant: Lith Haitham Nasif, Gainesville, FL (US)

(72) Inventor: Lith Haitham Nasif, Gainesville, FL (US)

( * ) Notice: Subject to any disclaimer, the term of this patent is extended or adjusted under 35 U.S.C. 154(b) by 672 days.

(21) Appl. No.: 17/734,117

(22) Filed: May 2, 2022

(65) Prior Publication Data

US 2022/0354470 A1 Nov. 10, 2022

Related U.S. Application Data

(60) Provisional application No. 63/184,305, filed on May 5, 2021.

(51) Int. Cl.
| | |
|---|---|
| *A61B 10/02* | (2006.01) |
| *A61B 17/3205* | (2006.01) |
| *A61B 17/00* | (2006.01) |

(52) U.S. Cl.
CPC .... *A61B 10/0266* (2013.01); *A61B 17/32053* (2013.01); *A61B 2017/00429* (2013.01)

(58) Field of Classification Search
CPC ...................... A61B 10/0266; A61B 17/32053
See application file for complete search history.

(56) References Cited

U.S. PATENT DOCUMENTS

| | | | | |
|---|---|---|---|---|
| 2004/0215217 A1* | 10/2004 | Banbury | ............ | A61B 17/0644 606/151 |
| 2005/0149092 A1* | 7/2005 | Dunn | ................. | A61B 10/0266 606/185 |
| 2007/0249960 A1* | 10/2007 | Williamson | ..... | A61B 17/32053 600/564 |
| 2008/0281226 A1* | 11/2008 | Peters | ................ | A61B 10/0266 600/567 |
| 2015/0057572 A1* | 2/2015 | Mendez-Coll | ......... | A61B 17/08 600/567 |
| 2015/0126903 A1* | 5/2015 | Wang | ................. | A61B 10/0266 600/567 |
| 2016/0058431 A1* | 3/2016 | Holzer | ............ | A61B 17/00491 600/570 |

\* cited by examiner

*Primary Examiner* — Daniel L Cerioni
(74) *Attorney, Agent, or Firm* — NORTON ROSE FULBRIGHT US LLP

(57) ABSTRACT

A punch biopsy apparatus to quickly and simply excise a sample of a chosen size and depth while preserving specimen morphology along with an independently operated mechanism to close the excision site. This design includes a body with a cylindrical needle to create a circular incision around the tissue, an independently rotated blade located within the cylindrical needle for excision at the base of the tissue, a plunger to allow release of the specimen, and a compartment for expulsion of skin glue, or another substance, configured to succinctly close the incision site to close the wound. This configuration allows punch biopsies to be performed efficiently with reduced technical skill, number of surgical instruments, and time required for the procedure.

18 Claims, 8 Drawing Sheets

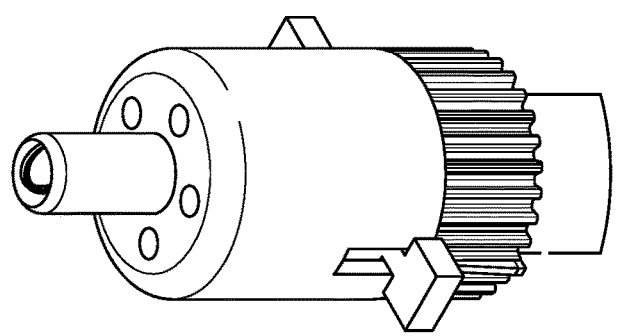
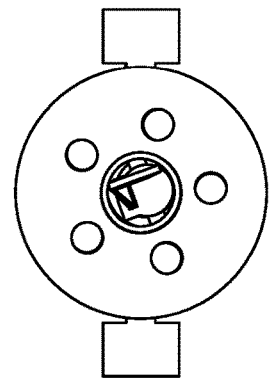
FIGURE 4
FIGURE 5
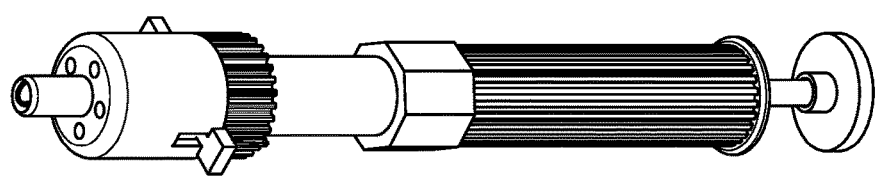
FIGURE 3
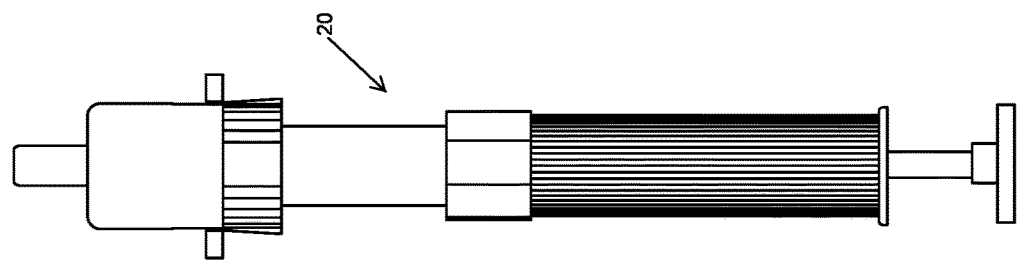
FIGURE 2
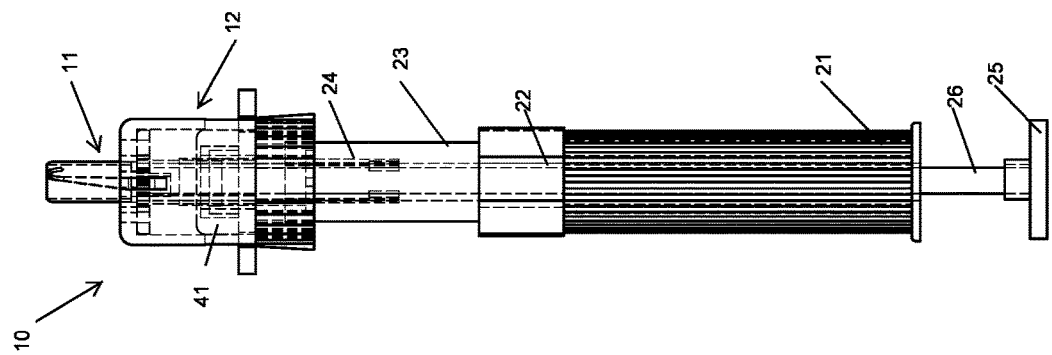
FIGURE 1

Rotate

Push Distally

Push Plunger Down

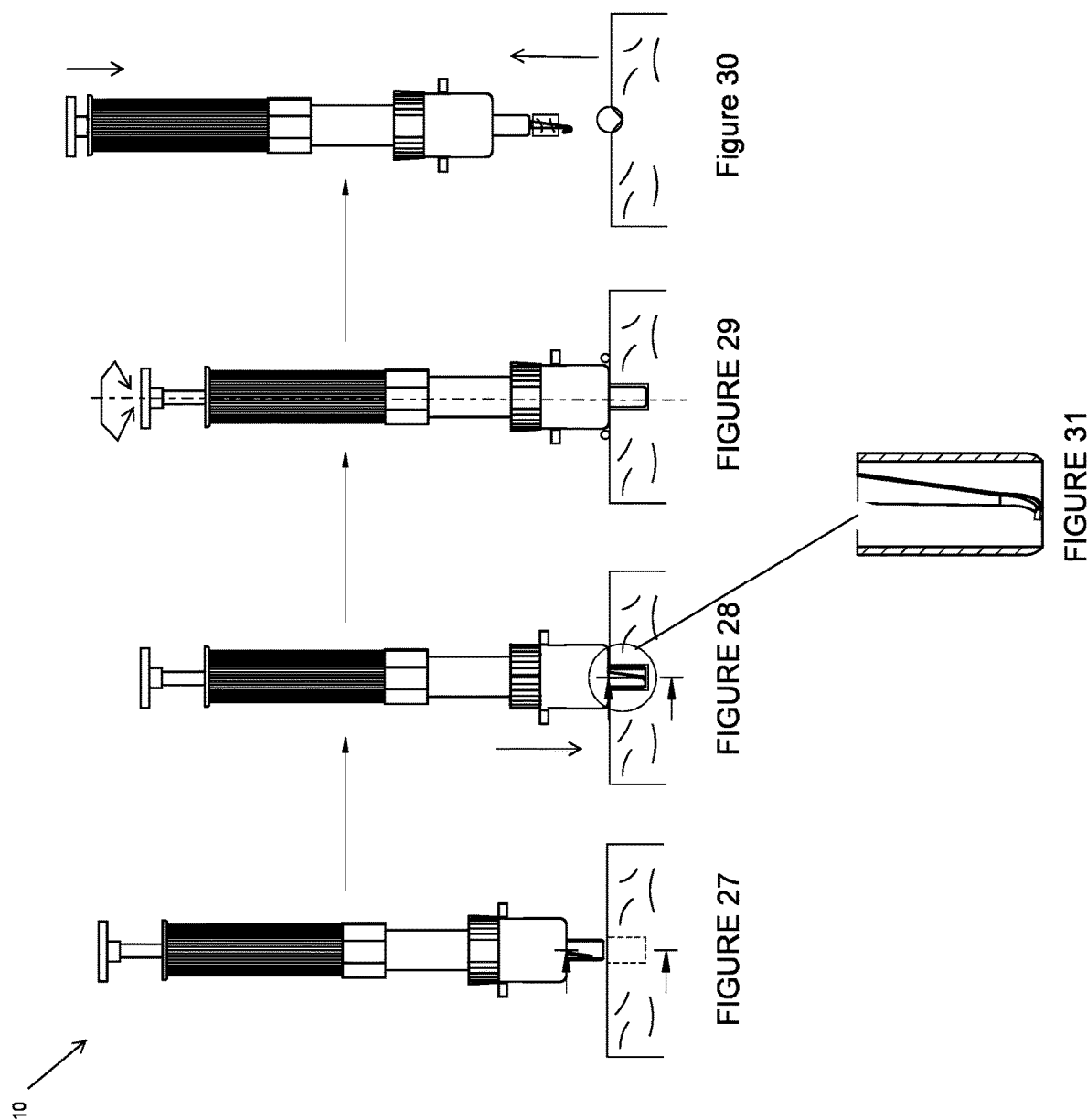

PUNCH BIOPSY APPARATUS AND ASSOCIATED METHOD(S)

CROSS REFERENCE TO RELATED APPLICATIONS

This application claims priority to U.S. Provisional Patent Application Ser. No. 63/184,305, filed May 5, 2021, and titled "PUNCH BIOPSY APPARATUS AND ASSOCIATED METHOD(S)," which is incorporated by reference herein in its entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE DISCLOSURE

Technical Field

Exemplary embodiment(s) of the present disclosure relate to punch biopsy and, more particularly, to a specially configured punch biopsy apparatus including an improved excision mechanism for effectively obtaining a skin tissue sample, as well as and an improved closure mechanism for succinctly closing the incision site.

Prior Art

Skin biopsy is extremely useful in diagnosing potential dermatological disorders. In fact, many incorrect diagnoses occur due to a failure to perform a skin biopsy, or an improperly executed biopsy. The most common technique used to obtain diagnostic, full-thickness dermatological samples is punch biopsy. The term "punch biopsy" refers to the nature of excising the suspect skin sample for analysis, which is akin to punching holes in a leather belt or punching holes in paper.

When faced with an abnormal skin lesion, physicians are often required to perform a biopsy to obtain a sample of the tissue. Types of skin biopsies include shave, excisional, and punch, and the samples provided by each differ in size and depth. Punch biopsies are the primary technique used to acquire full-thickness specimens because they obtain the epidermis, the dermis and the subcutaneous tissue. Punch biopsies, however, are technique-dependent and require multiple surgical instruments to perform. Two aspects of the procedure, namely the depth of the punch (sample thickness) and the mechanical handling of the specimen can particularly affect the quality of the sample as inadequate sample depth or mechanically induced crush artifact can prevent pathologists from making accurate diagnoses.

The current procedure can be divided into three phases. There is the 'punch' phase during which the punch cylindrical blade creates a circular incision in the skin. This is followed by the 'excision' phase where the sample is transected or "cut" at its base and finally by the 'closure' phase where the wound is sutured. For the punch phase, damage to underlying artery or nerve could be done if the depth of the punch is not regulated. In the excision phase, integrity of the skin sample could be compromised if the sample is severed traumatically or the tissue is not excised to an adequate depth. An inadequate sample undermines the diagnosis done by the pathologist and a repeat procedure must be performed. The closure phase is the most time-consuming phase of the procedure and requires physicians to handle sharp objects to and patients to return for a follow up appointment to remove the suture. Furthermore, the current clinical set up requires many instruments all of which take time to sterilize using an autoclave and increase the cost of a punch biopsy kit.

Accordingly, a need remains for punch biopsy apparatus in order to overcome some of the above-noted shortcomings. The exemplary embodiment(s) satisfy such a need by a specially configured punch biopsy apparatus that is convenient and easy to use, lightweight yet durable in design, versatile in its applications, and configured to provide an improved excision mechanism for effectively obtaining a skin tissue sample, as well as and an improved closure mechanism for succinctly closing the excision site.

SUMMARY OF THE INVENTION

A punch biopsy is the primary method used by physicians to achieve a full-thickness tissue specimen to assess and diagnose a myriad of dermatological conditions. Yet, the currently used punch biopsy method requires a variety of tools as well as a significant amount of time and skill to perform the procedure correctly. These barriers limit a physician's ability to perform a punch biopsy during an office visit, and, if performed, many collected specimens are not suitable for pathological analysis.

This invention is comprised of three main components that incorporate the rotational incision, excision, specimen retrieval, and closure aspects of the procedure into one device. These components include a cylindrical needle and needle holder used to create a circular incision around the tissue, a blade located within the cylindrical needle that can rotate independently of the coring needle to allow proper depth excision of the tissue that is attached to a movable plunger to allow release of the specimen without disrupting tissue morphology, and a compartment for skin glue that can be used to expel the glue around the procedure site without lifting the device from the skin for rapid and sutureless closer of the wound. The design creates a simpler, quicker, and more consistent method of obtaining punch biopsies, allowing the procedure to be accessible to more doctors and patients, while also reducing the number of materials needed in a punch biopsy kit.

This summary is intended to provide a brief and simplified description of the device that is further elaborated on in the detailed description. The description and examples in the summary are not intended to define or limit the scope of the disclosure in any way.

BRIEF DESCRIPTION OF THE SEVERAL VIEWS OF THE DRAWING

The novel features believed to be characteristic of the exemplary embodiment(s) are set forth with particularity in the appended claims. The disclosure itself, however, both as to its organization and method of operation, together with further objects and advantages thereof, may best be understood by reference to the following description taken in connection with the accompanying drawings in which:

The figures generally include various perspective/elevational view(s) showing a specially configured punch biopsy apparatus including an improved incision mechanism for effectively obtaining a skin tissue sample, as well as and an improved closure mechanism for succinctly closing the incision site, in accordance with non-limiting exemplary embodiment(s) of the present disclosure.

FIG. 1 is a perspective view of an exemplary punch biopsy apparatus in accordance with the present invention with the dashed lines indicating parts of the design that are normally hidden from view.

FIGS. 2-3 show a perspective view of an exemplary punch biopsy apparatus in accordance with the present invention with the plunger and closure mechanism fully retracted.

FIG. 4 is an enlarged perspective view of the top portion of an exemplary punch biopsy apparatus in accordance with the present invention.

FIGS. 27-30 show perspective views of an exemplary punch biopsy apparatus in accordance with the present invention and a representation of skin with each arrow indicating the next step of the use of the device needed to obtain a tissue specimen.

FIG. 31 illustrates an enlarged perspective view of the blade within the coring needle used to excise the base of the sample in an exemplary punch biopsy apparatus in accordance with the present invention.

DETAILED DESCRIPTION OF THE DISCLOSURE

The non-limiting exemplary embodiment(s) will now be described more fully hereinafter with reference to the accompanying drawings, in which a preferred embodiment of the disclosure is shown. Such exemplary embodiment(s) may, however, be embodied in many different forms and should not be construed as limited to the embodiment set forth herein. Rather, these embodiment(s) are provided so that this application will be thorough and complete, and will fully convey the true scope of the disclosure to those skilled in the art.

The below disclosed subject matter is to be considered illustrative, and not restrictive, and any appended claim(s) are intended to cover all such modifications, enhancements, and other embodiment(s) which fall within the true scope of the non-limiting exemplary embodiment(s). Thus, to the maximum extent allowed by law, the scope of the non-limiting exemplary embodiment(s) is to be determined by the broadest permissible interpretation of the claim(s) and their equivalents, and shall not be restricted or limited by the foregoing detailed description.

References in the specification to "an exemplary embodiment", "an embodiment", "a preferred embodiment", "an alternative embodiment" and similar phrases mean that a particular feature, structure, or characteristic described in connection with the embodiment(s) is included in at least an embodiment of the disclosure. The appearances of the phrase "a non-limiting exemplary embodiment" in various places in the specification are not necessarily all meant to refer to the same embodiment.

Figure 8:
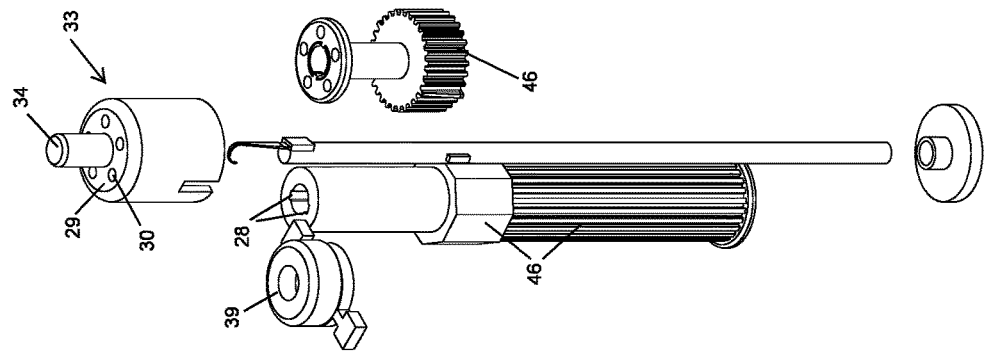
FIGS. 6-8 show perspective views of an exemplary punch biopsy apparatus in accordance with the present invention with the different components of the device separated for individual view in their respective positions in space.
Figure 7:
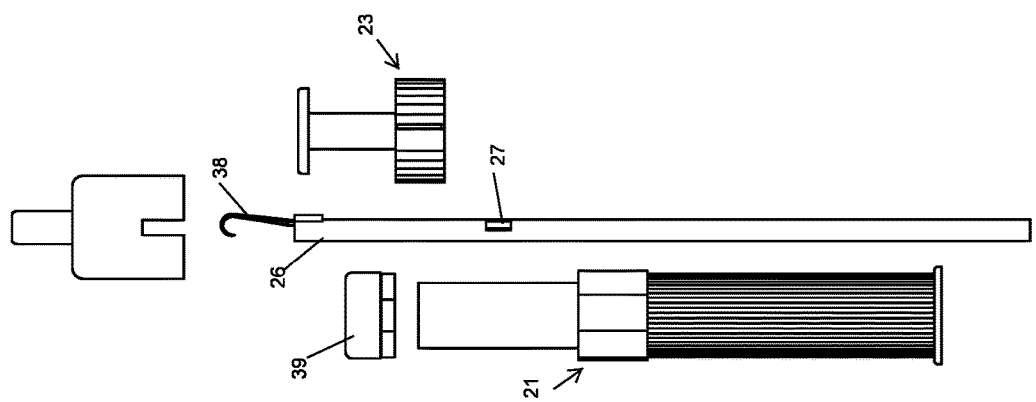
Figure 6:
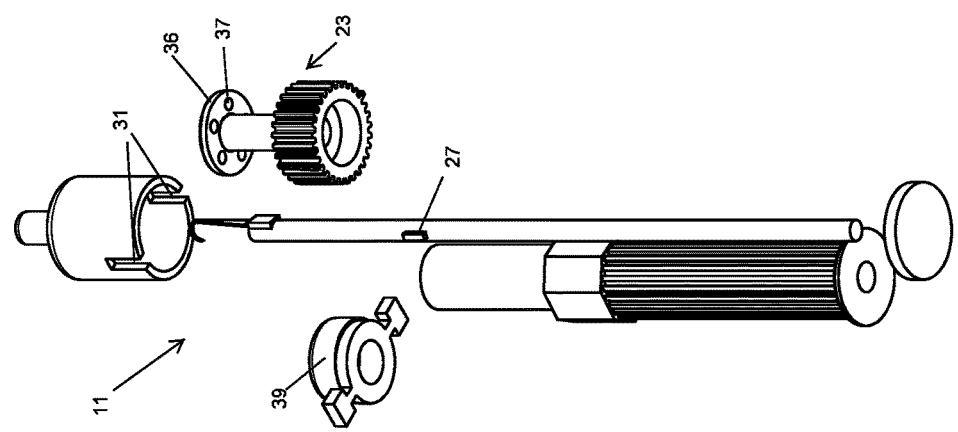
Figure 14:
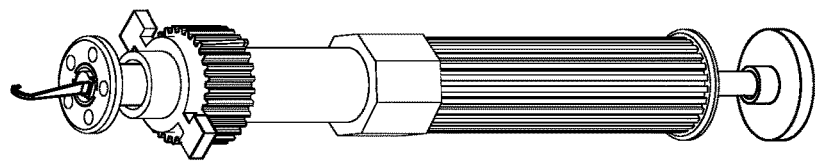
FIGS. 9-14 show perspective views of an exemplary punch biopsy apparatus in accordance with the present invention with the coring needle and fluid holder pieces removed to show the inside of the top portions of the device.
Figure 13:
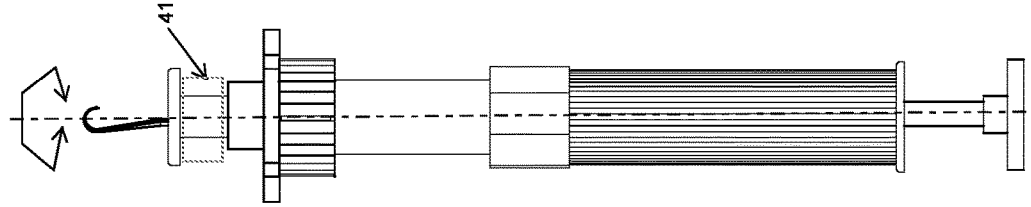
Figure 12:
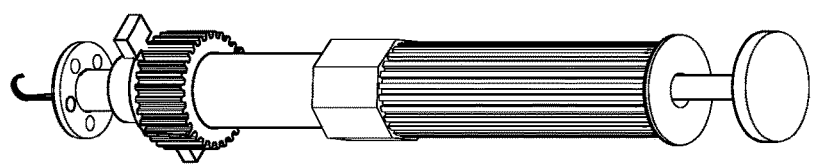
Figure 11:
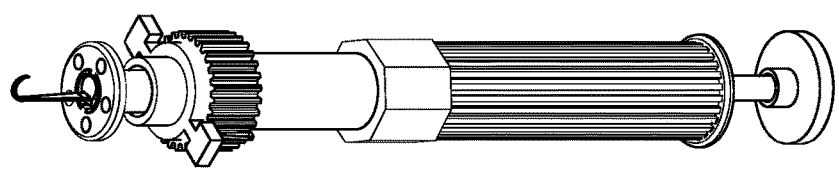
Figure 10:
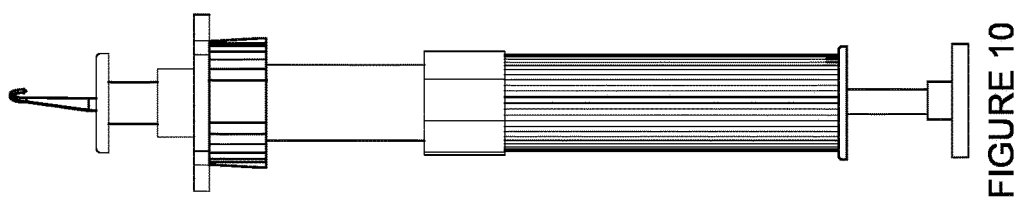
Figure 9:
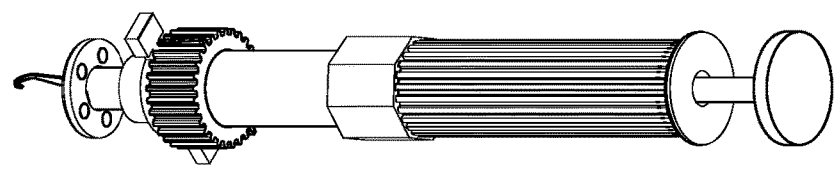
Figure 19:
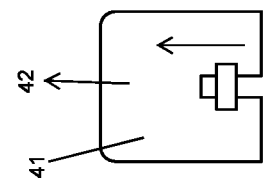
FIGS. 15-22 show enlarged perspective views of the closure mechanism of an exemplary punch biopsy apparatus in accordance with the present invention with FIGS. 19-22 representing the closure mechanism being pushed distally to expel the fluid in the container.
Figure 20:
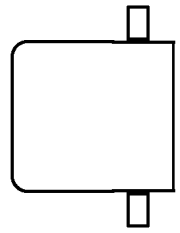
Figure 21:
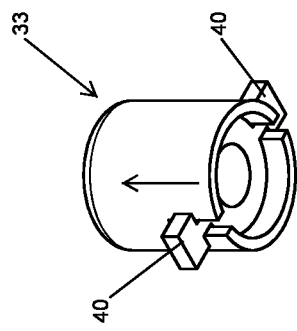
Figure 22:
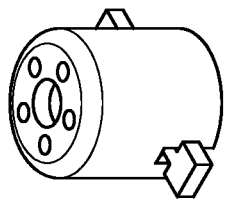
Figure 17:
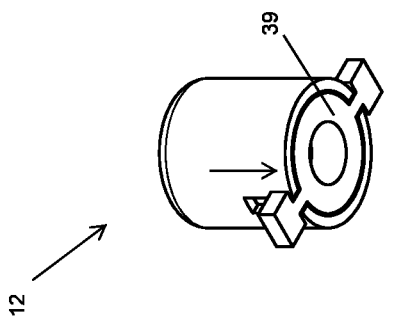
Figure 18:
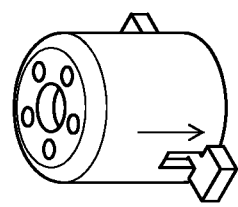
Figure 15:
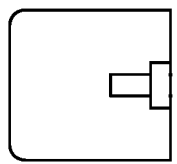
Figure 16:
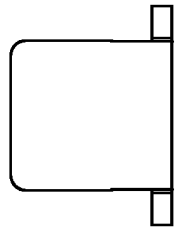
Figure 26:
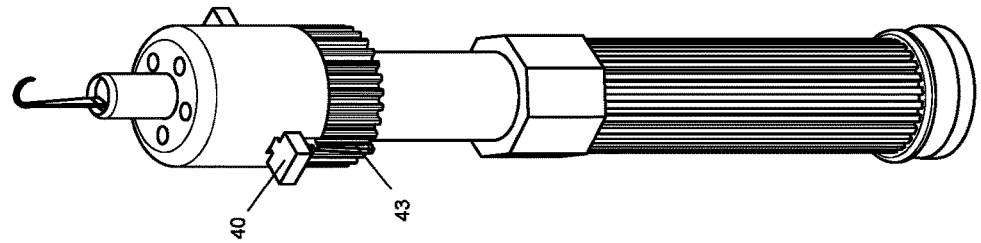
FIGS. 23-26 show perspective views of an exemplary punch biopsy apparatus in accordance with the present invention with FIGS. 25-26 illustrating the plunger pushed down which is done to release the collected specimen.
Figure 25:
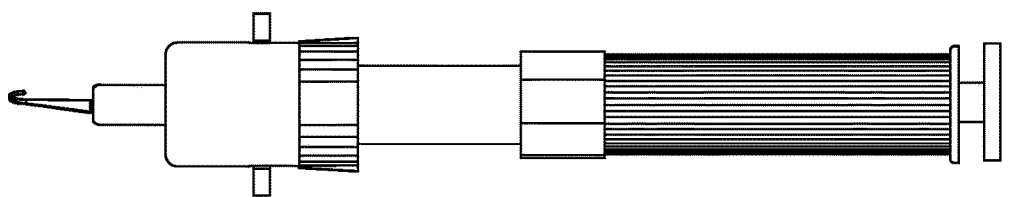
Figure 24:
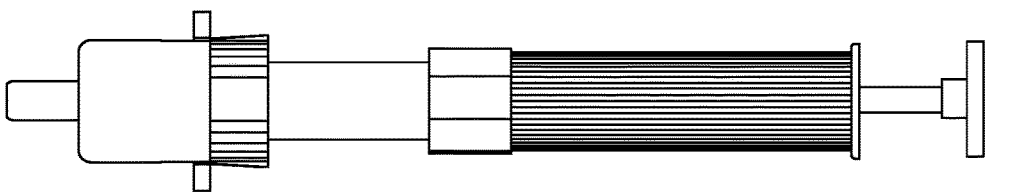
Figure 23:
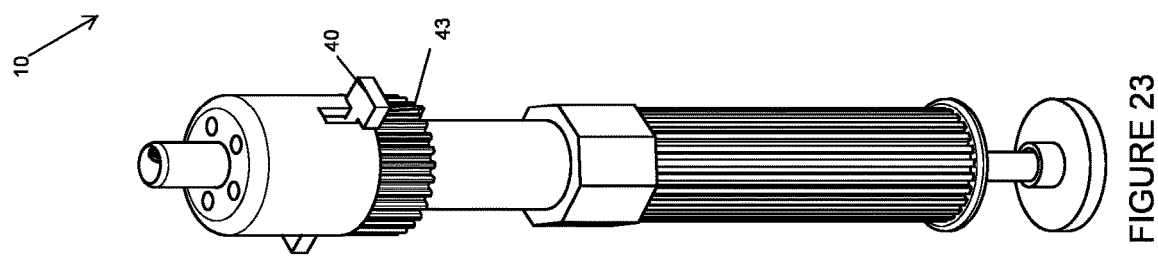
Figure 32:
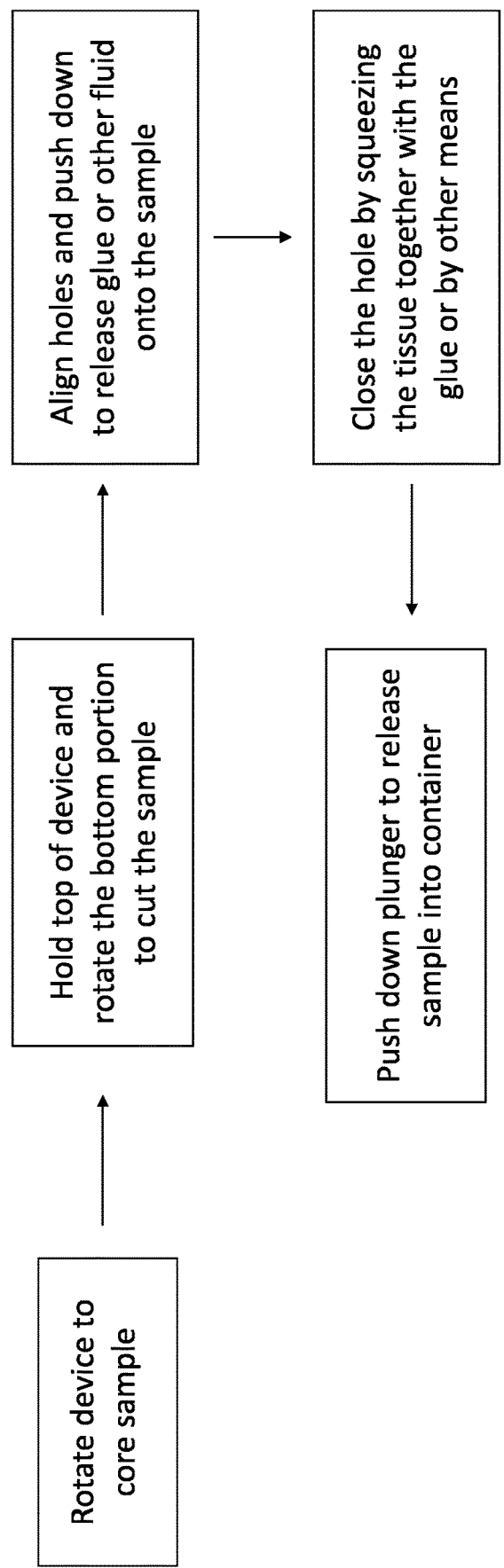
FIG. 32 is a diagram with descriptions of the use of an exemplary punch biopsy apparatus in accordance with the present invention which correlate to the steps illustrated in FIGS. 27-30.
Figure 36:
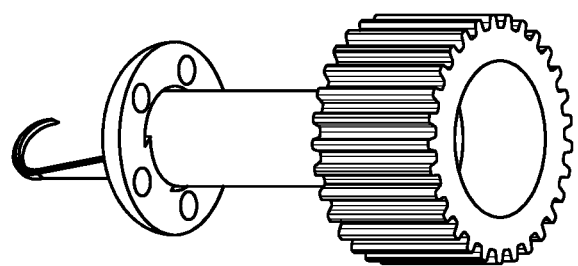
FIGS. 33-36 show enlarged perspective views of an additional exemplary embodiment in which the cutting blade is affixed to the grip and rotator rather than the shaft of the plunger. In both embodiments the blade rotates independently of the coring needle to excise the base of the tissue.
Figure 35:
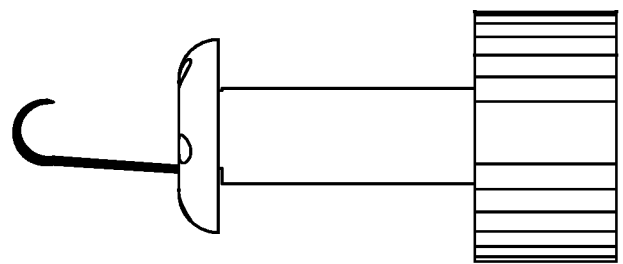
Figure 34:
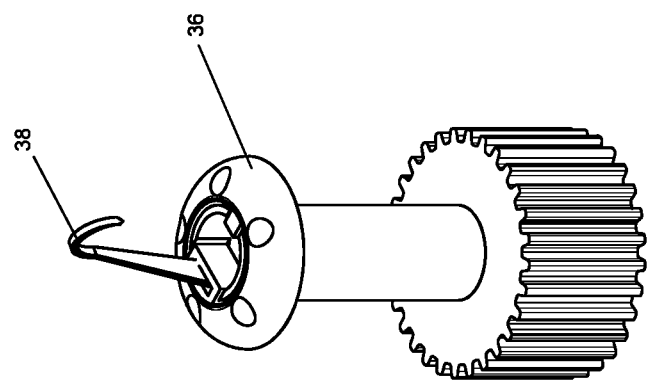
Figure 33:
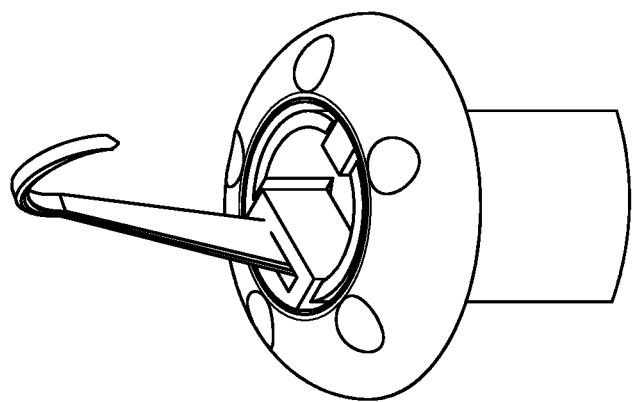

A non-limiting exemplary embodiment(s) of the present disclosure is referred to generally in FIGS. 1-36 and is/are intended to provide a specially configured punch biopsy apparatus 10 including an improved incision mechanism 11 for effectively obtaining and releasing a skin tissue sample without damaging the tissue, as well as an improved closure mechanism 12 for succinctly closing the incision site. It should be understood that the exemplary embodiment(s) may be used to acquire a variety of tissue samples, and should not be limited to any particular tissue sample described herein.

Referring to FIGS. 1-36 in general, in a non-limiting exemplary embodiment(s), the punch biopsy apparatus 10 includes a body 20 including an excision mechanism 11 configured to effectively create an incision at the base of the excision site as well as obtain and release a skin tissue sample from the excision site, a closure mechanism 12 configured to succinctly close the excision site, and a distal section 33 detachably coupled to each of the excision mechanism 11 and the closure mechanism 12. Advantageously, the excision mechanism 11 is independently operable from the closure mechanism 12.

In a non-limiting exemplary embodiment, the body 20 further includes a primary grip section 21 having a first axial bore 22 extended along an entire longitudinal length thereof, an auxiliary grip section 23 having a second axial bore 24 extending along an entire longitudinal length thereof and being coaxially registered with the first axial bore 22, and a plunger 25 having an elongated rectilinear shaft 26 slidably interfitted through the first axial bore 22 and the second axial bore 24.

In a non-limiting exemplary embodiment, each of the closure mechanism 12 and the excision mechanism 11 is operably coupled to the shaft 26 and the auxiliary grip section 23.

In a non-limiting exemplary embodiment, the shaft 26 includes a circumferential outer surface having a pair of diametrically opposed fingers 27 protruding outwardly and away therefrom. Advantageously, the primary grip section 21 includes a pair of diametrically opposed slots 28 configured to slidably receive the fingers 27 therethrough and thereby cause the shaft 26, the primary grip section 21, and the auxiliary grip section 23 to contemporaneously articulate in clockwise and counter clockwise rotational directions.

In a non-limiting exemplary embodiment, the distal section 33 includes a distal end 29 having a plurality of first apertures 30 juxtaposed in an annular configuration, and a proximal end 31 having a pair of diametrically opposed slots 32.

In a non-limiting exemplary embodiment, the excision mechanism 11 includes a coring implement 34 statically affixed to the distal end 29 of the distal section 33 and centrally disposed relative to the annular configuration.

In a non-limiting exemplary embodiment, the closure mechanism 12 includes a disc-shaped guide member 36 statically coupled to the auxiliary grip section 23 and has a plurality of second apertures 37 selectively rotated and aligned with the first apertures 30 at the distal section 33.

In a non-limiting exemplary embodiment, the excision mechanism 11 further includes a cutting implement 38 statically affixed to one of: the shaft 26 (see FIGS. 6-8) and the disc-shaped guide member 36 (see FIGS. 33-36).

In a non-limiting exemplary embodiment, the coring implement 34 is suitably sized and shaped for receiving a corresponding one of the cutting implement 38 therethrough.

In a non-limiting exemplary embodiment, the closure mechanism 12 further includes an actuator 39 in linear reciprocal communication with the auxiliary grip section 23 wherein the actuator 39 has a pair of diametrically opposed flanges 40 oriented perpendicular to the longitudinal length of the auxiliary grip section 23, a resilient gasket 41 intermediately situated between the disc-shaped guide member 36 and the actuator 39, and a viscous sealing agent 42 housed distally of the resilient gasket 41 and contained within the distal section 33. Advantageously, when the first apertures 30 and the second apertures 37 are aligned, the viscous sealing agent 42 is urged distally through the distal end 29 as the actuator 39 is linear displaced distally within the slots 28 of the distal section 33, respectively.

In a non-limiting exemplary embodiment, the viscous sealing agent 42 is glue.

In a non-limiting exemplary embodiment, the coring implement 34 may be a hollow cylindrical needle. The cutting implement 38 may be a hook-shaped blade.

In a non-limiting exemplary embodiment, the shaft 26 is statically connected to the cutting implement 38 and rotated in sync therewith.

In a non-limiting exemplary embodiment, the plunger 25 is selectively and linearly reciprocated within the first axial bore 22 and the second axial bore 24 and thereby causes the cutting implement 38 to the coring implement 34, respectively.

In a non-limiting exemplary embodiment, each of the primary grip section 21, the auxiliary grip section 23, and the cutting implement 38 are contemporaneously rotated relative to a stationary position of the distal end 29 and the coring implement 34.

In a non-limiting exemplary embodiment, the auxiliary grip section 23 further includes a peripheral outer surface including a plurality of juxtaposed ribs 43 disposed therealong. Advantageously, a selected pair of the ribs 43 each is obliquely angled and outwardly flared relative to remaining ones of the ribs 43 such that the first apertures 30 are aligned with the second apertures 37 when the flanges 40 of the actuator 39 are aligned with the selected pair of ribs 43.

In a non-limiting exemplary embodiment, an end cap (not shown) is removably attached to the distal section 33.

In a non-limiting exemplary embodiment, each of the auxiliary grip section 23 and the primary grip section 21 has a corrugated outer peripheral surface configured provide a friction-inducing surface 46.

In a non-limiting exemplary embodiment, the cutting implement may be anchored to a support member 49 (intermediary member) affixed to the shaft 26.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the disclosure of the application, nor is it intended to be limiting as to the scope of the disclosure in any way.

While the disclosure has been described with respect to certain specific embodiment(s), it will be appreciated that many modifications and changes may be made by those skilled in the art without departing from the spirit of the disclosure. It is intended, therefore, by the description hereinabove to cover all such modifications and changes as fall within the true spirit and scope of the disclosure. In particular, with respect to the above description, it is to be realized that the optimum dimensional relationships for the parts of the exemplary embodiment(s) may include variations in size, materials, shape, form, function and manner of operation.

What is claimed as new and what is desired to secure by Letters Patent of the United States is:

1. A punch biopsy apparatus comprising:
   a body including:
      an excision mechanism configured to effectively create an excision at an excision site as well as obtain and release a skin tissue sample from the excision site;
      a closure mechanism configured to succinctly close the excision site; and
      a distal section detachably coupled to each of said excision mechanism and said closure mechanism;
   wherein said excision mechanism is independently operable from said closure mechanism.

2. The punch biopsy apparatus of claim 1, wherein said body further comprises:
   a primary grip section having a first axial bore extended along an entire longitudinal length thereof;
   an auxiliary grip section having a second axial bore extending along an entire longitudinal length thereof and being coaxially registered with said first axial bore; and
   a plunger having an elongated rectilinear shaft slidably interfitted through said first axial bore and said second axial bore.

3. The punch biopsy apparatus of claim 2, wherein each of said closure mechanism and said excision mechanism is operably coupled to said shaft and said auxiliary grip section.

4. The punch biopsy apparatus of claim 3, wherein said shaft comprises: a circumferential outer surface having a pair of diametrically opposed fingers protruding outwardly and away therefrom;
   wherein said primary grip section includes a pair of diametrically opposed slots configured to slidably receive said fingers therethrough and thereby cause said shaft, said primary grip section, and said auxiliary grip section to contemporaneously articulate in clockwise and counter clockwise rotational directions.

5. The punch biopsy apparatus of claim 4, wherein distal section comprises:
   a distal end having a plurality of first apertures juxtaposed in an annular configuration; and a proximal end having a pair of diametrically opposed slots.

6. The punch biopsy apparatus of claim 5, wherein said excision mechanism comprises:
   a coring implement statically affixed to said distal end of said distal section and centrally disposed relative to said annular configuration.

7. The punch biopsy apparatus of claim 6, wherein said closure mechanism comprises:
a disc-shaped guide member statically coupled to said auxiliary grip section and having a plurality of second apertures selectively rotated and aligned with said first apertures at said distal section.

8. The punch biopsy apparatus of claim 7, wherein said excision mechanism further comprises:
a cutting implement statically affixed to one of: said shaft and said disc-shaped guide member.

9. The punch biopsy apparatus of claim 8, wherein said coring implement is suitably sized and shaped for receiving a corresponding one of said cutting implement therethrough.

10. The punch biopsy apparatus of claim 8, wherein said closure mechanism further comprises:
an actuator in linear reciprocal communication with said auxiliary grip section, said actuator having a pair of diametrically opposed flanges oriented perpendicular to the longitudinal length of said auxiliary grip section;
a resilient gasket intermediately situated between said disc-shaped guide member and said actuator; and
a viscous sealing agent housed distally of said resilient gasket and contained within said distal section;
wherein, when said first apertures and said second apertures are aligned, said viscous sealing agent is urged distally through said distal end as said actuator is linear displaced distally within said slots of said distal section, respectively.

11. The punch biopsy apparatus of claim 10, wherein said viscous sealing agent is glue.

12. The punch biopsy apparatus of claim 8, wherein said coring implement is a hollow cylindrical needle; wherein said cutting implement is a hook-shaped blade.

13. The punch biopsy apparatus of claim 8, wherein said shaft is statically connected to said cutting implement and is configured to be rotated in sync therewith.

14. The punch biopsy apparatus of claim 8, wherein said plunger is configured to be selectively and linearly reciprocated within said first axial bore and said second axial bore and thereby causes said cutting implement to selectively egress and ingress said coring implement, respectively.

15. The punch biopsy apparatus of claim 8, wherein each of said primary grip section, said auxiliary grip section, and said cutting implement are configured to be contemporaneously rotated relative to a stationary position of said distal end and said coring implement.

16. The punch biopsy apparatus of claim 10, wherein said auxiliary grip section further comprises:
a peripheral outer surface including a plurality of juxtaposed ribs disposed therealong;
wherein a selected pair of said ribs each is obliquely angled and outwardly flared relative to remaining ones of said ribs;
wherein said first apertures are aligned with said second apertures when said flanges of said actuator are aligned with said selected pair of ribs.

17. The punch biopsy apparatus of claim 1, further comprising: an end cap removably attached to said distal section.

18. The punch biopsy apparatus of claim 1, wherein each of said auxiliary grip section and said primary grip section has a corrugated outer peripheral surface configured provide a friction-inducing surface.

* * * * *